(12) United States Patent
Fainshtein

(10) Patent No.: US 9,830,720 B2
(45) Date of Patent: Nov. 28, 2017

(54) GRAPHICS CONTROL DURING FLOW CYTOMETRY EVENT GATING

(71) Applicant: Becton, Dickinson and Company, Franklin Lakes, NJ (US)

(72) Inventor: Alexander Fainshtein, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 149 days.

(21) Appl. No.: 14/843,269

(22) Filed: Sep. 2, 2015

(65) Prior Publication Data

US 2017/0061657 A1 Mar. 2, 2017

(51) Int. Cl.
| | |
|---|---|
| *G06T 11/20* | (2006.01) |
| *G06F 3/14* | (2006.01) |
| *G09G 5/36* | (2006.01) |
| *G01N 15/14* | (2006.01) |
| *G01N 15/10* | (2006.01) |

(52) U.S. Cl.
CPC .............. *G06T 11/206* (2013.01); *G06F 3/14* (2013.01); *G09G 5/363* (2013.01); *G01N 15/1429* (2013.01); *G01N 2015/1006* (2013.01); *G01N 2015/1402* (2013.01)

(58) Field of Classification Search
None
See application file for complete search history.

(56) References Cited

U.S. PATENT DOCUMENTS

| | | | |
|---|---|---|---|
| 4,845,653 | A | 7/1989 | Conrad et al. |
| 5,627,040 | A | 5/1997 | Bierre et al. |
| 5,739,000 | A | 4/1998 | Bierre et al. |
| 5,795,727 | A | 8/1998 | Bierre et al. |
| 5,962,238 | A | 10/1999 | Sizto et al. |
| 6,014,904 | A | 1/2000 | Lock |
| 6,944,338 | B2 | 9/2005 | Lock et al. |
| 2012/0245889 | A1 | 9/2012 | Zhu et al. |
| 2013/0229412 | A1* | 9/2013 | Suzuki ................... G01N 15/14 345/419 |
| 2014/0240314 | A1* | 8/2014 | Fukazawa ............. G06T 11/206 345/419 |

OTHER PUBLICATIONS

Bauer et al. (eds.), Clinical Flow Cytometry: Principles and Applications, Williams & Wilkins (Jan. 1993).
Jaroszeski et al. (eds.), Flow Cytometry Protocols, Methods in Molecular Biology No. 91, Humana Press (Nov. 1997).
Landay et al. (eds.), Clinical Flow Cytometry, Annals of the New York Academy of Sciences vol. 677 (Mar. 1993).

(Continued)

*Primary Examiner* — Peter Hoang
(74) *Attorney, Agent, or Firm* — Knobbe Martens Olson & Bear LLP

(57) ABSTRACT

When manually drawing gates on plots of flow cytometric data, how the underlying data is rendered can cause inaccuracies and/or inefficiencies in the drawing. The present application is directed to graphics control features for dynamically adjusting attributes of the plot such as event color or plot style (e.g., dot plot, contour plot) while drawing a gate. The adjustments may be triggered by the gate, by the area being gated, or a trigger (e.g., mouse or key stroke event) while drawing the gate.

20 Claims, 8 Drawing Sheets

(56) References Cited

OTHER PUBLICATIONS

Ormerod (ed.), Flow Cytometry: A Practical Approach, Oxford Univ. Press (Aug. 1994).
Pawley (ed.), Handbook of Biological Confocal Microscopy, 2nd Edition, Plenum Press (Aug. 1989).
Shapiro Practical Flow Cytometry, 4th ed., Wiley-Liss (Jul. 2003).

* cited by examiner

GRAPHICS CONTROL DURING FLOW CYTOMETRY EVENT GATING

BACKGROUND

Technical Field

This disclosure relates to controlling graphic displays, and in particular to control of graphic displays during gating and gate manipulations of cytometric data such as flow cytometer populations.

Background

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Cytometers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; and 6,944,338; and U.S. Pat. Pub. No. 2012/0245889, each incorporated herein by reference.

Gating is used to help make sense of the large quantity of data that may be generated from a sample. Given the large quantities of data presented for a given sample, there exists a need to efficiently control the graphical display of the data.

SUMMARY

The systems, methods, and devices of the disclosure each have several innovative aspects, no single one of which is solely responsible for the desirable attributes disclosed herein.

In one innovative aspect a graphics control device for display of cytometric events is provided. The graphics control device includes an input device port configured to receive messages from input devices. The graphics control device includes an event listener in data communication with the input device port. The event listener is configured to process the messages received from the input devices. The graphics control device further includes a display adjustment circuit in data communication with the event listener. The display adjustment circuit is configured to identify an adjustment to a graphic display of flow cytometric events in response to a message received from an input device. The graphics control device further includes a plot generator in data communication with the display adjuster. The plot generator is configured to generate a computer displayable graphic representation of the flow cytometry events. The plot generator modifies a gate around a population within the graphic display when adjusting the graphic display using the adjustment identified by the display adjustment circuit.

In some implementations, the graphics control device includes a memory for storing a display setting for graphically plotting events upon receipt of a message including a triggering event. The display setting may indicate at least one of: a plot display size, a plot type, event display coloring, or a quantity of events to display. In such implementations, the plot generator may be further configured to retrieve the display setting for the triggering event and generate the computer displayable graphic representation using the display setting.

In some implementations of the graphics control device, the memory may be configured to store the display setting that further indicates a target event display density. The plot generator may be configured to generate the computer displayable graphic representation including a display of the flow cytometric events according to the stored target event display density.

The plot generator may be configured to present events within the gate for display differently from other events in the flow cytometry events according to a first display setting via a first computer-displayable graphic representation. The plot generator may also present all events of the flow cytometry events for display according to a second display setting via a second computer displayable graphic representation.

In some implementations, the plot generator is configured to present events within the gate for display according to a first display setting via a first computer-displayable graphic representation. Via a second representation, the plot generator may present all of the flow cytometry events displayed according to a second plot display configuration.

It may be desirable for the plot generator to be configured to, in response to a triggering event, generate an expanded area by expanding an area of a first computer displayable graphic representation identified by the gate around the population by an expansion factor. The plot generator may identify a quantity of events to display via a second computer displayable graphic representation such that events displayed within the gate match a target event display density and then select the quantity of events. The plot generator may then include a visual indicator for each event selected on the second computer displayable graphic representation. Some implementations of the graphics control may include a plot generator that is further configured to generate a reduced area by reducing the area of the first computer displayable graphic representation identified by the gate around the population by a reduction factor. In such implementations, an area between the expanded area and the reduction area includes events displayed at the target event display density via the second computer displayable graphic representation. Each event included in the flow cytometry events may be associated with a sequence number. The plot generator may select the quantity of events by sequentially selecting events, from the flow cytometry events, beginning with the first sequence number until the quantity of events is obtained. The plot generator may be configured to select the quantity of events by other methods, in combination or in the alternative. For example, the plot generator may randomly select events, from the flow cytometry events, until the quantity of events is obtained. As another example, the plot generator may select via uniform sampling of the flow cytometry events until the quantity of events is obtained.

If the flow cytometry data does not include enough events to reach the identified quantity, the plot generator may be configured to increase the size of visual indicators for events within the gate such that a display area within the gate matches the target event display density for the second computer displayable graphic representation.

In another innovative aspect, a method of controlling graphic display of cytometric events is described. The method includes providing a graphic display including a first plot of flow cytometry events. The method includes rendering a gate around a population of cytometric events shown by the graphic display, the gate overlaid upon the first plot. The method further includes receiving a gate selection signal identifying the gate from a first input device. The method includes, while the gate is selected, receiving a triggering event from a second input device and, in response to the triggering event, replacing the first plot with a second plot while modifying the gate on the graphic display.

Some implementations of the method include retrieving a display setting for graphically plotting events upon receipt of the triggering event. In such implementations, replacing the first plot with the second plot includes obtaining the display setting for the triggering event and generating the second plot using the display setting.

The display setting may further indicate a target event display density. The target event display density may be less than or equal to a density of events shown in the first plot. In such instances, generating the second plot includes a display of the flow cytometric events according to the target event display density.

In some implementations of the method, events within the gate are displayed differently from other events in the flow cytometry events according to a first display setting via the first plot. All events of the flow cytometry events may then be displayed according to a second display setting via the second plot.

In some implementations of the method, events within the gate are displayed according to a first display setting via the first plot and all of the flow cytometry events are displayed according to a second plot display configuration via the second plot.

The method may include, in further response to the triggering event, generating an expanded area by expanding an area of the first plot identified by the gate around the population by an expansion factor. A quantity of events to display via the second plot such that events displayed within the gate match a target event display density may be identified and the quantity of events selected. The method may include a visual indicator for each event selected on the second plot. Some implementations of the method may include generating a reduction area by reducing the area of the first plot identified by the gate around the population by a reduction factor. An overlapping area between the expanded area and the reduction area may include events displayed at the target event display density via the second plot.

The method may include one or more features for selecting quantities of events. For example, selecting the quantity of events may include randomly selecting events, from the flow cytometry events, until the quantity of events is obtained, and/or selecting via uniform sampling of the flow cytometry events until the quantity of events is obtained.

If the flow cytometry data does not include enough events to reach the quantity, including the visual indicator may include increasing the size of visual indicators for events within the gate such that a display area within the gate matches the target event display density via the second plot.

In a further innovative aspect, an apparatus is provided. The apparatus includes a flow cytometer configured to acquire flow cytometric events. The apparatus includes one or more processors in communication with the flow cytometer. The one or more processors are configured to provide a graphic display including a first plot of flow cytometry events. The one or more processors are further configured to render a gate around a population of cytometric events shown by the graphic display, the gate overlaid upon the first plot. The one or more processors are further configured to receive a gate selection signal identifying the gate from a first input device. While the gate is selected, the processors are configured to receive a triggering event from a second input device and, in response to the triggering event, replace the first plot with a second plot while modifying the visual indicator. In one innovative aspect, a method for generating a contour, a tangible machine readable storage device having computer-executable instructions stored thereon for generating a contour, and a system for generating a contour are described with reference to the accompanying drawings.

DETAILED DESCRIPTION

Figure 1:
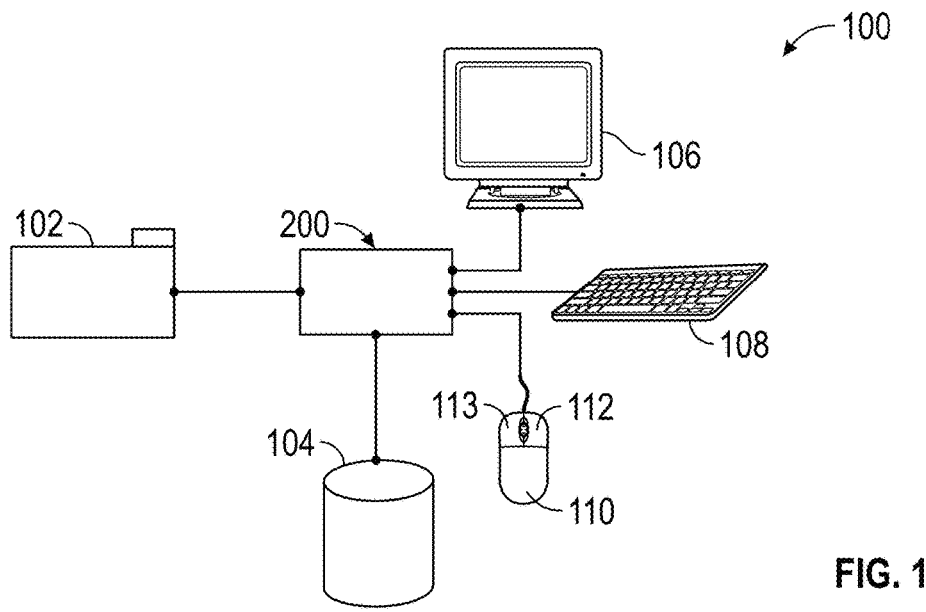
FIG. 1 shows a functional block diagram for one example of a graphics control system for analyzing and displaying cytometric events.

When drawing gates on plots of flow cytometric data, how the underlying data is rendered can cause inaccuracies and/or inefficiencies in the drawing. In one respect, aspects of the present application are directed to graphics control features for dynamically adjusting attributes of the plot such as event color or plot style (e.g., dot plot, contour plot) while drawing a gate. The adjustments may be triggered by the gate, by the area being gated, or a trigger (e.g., mouse or key stroke event) while drawing the gate.

As used herein, "system," "instrument," "apparatus," and "device" generally encompass both the hardware (e.g., mechanical and electronic) and, in some implementations, associated software (e.g., specialized computer programs for graphics control) components.

As used herein, an "event" generally refers to the data measured from a single particle, such as cells or synthetic particles. Typically, the data measured from a single particle include a number of parameters, including one or more light scattering parameters, and at least one fluorescence intensity parameters. Thus, each event is represented as a vector of parameter measurements, wherein each measured parameter corresponds to one dimension of the data space.

As used herein, a "population", or "subpopulation" of particles, such as cells or other particles, generally refers to a group of particles that possess optical properties with respect to one or more measured parameters such that measured parameter data form a cluster in the data space. Thus, populations are recognized as clusters in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters.

As used herein, a "gate" generally refers to a boundary identifying a subset of data of interest. In cytometry, a gate may bound a group of events of particular interest. As used herein, "gating" generally refers to the process of defining a gate for a given set of data.

A dot plot may be used to illustrate cytometric events. For example, FIG. 9, discussed further below, shows a dot plot of cytometric events. A portion of the cytometric events are surrounded by a gate 902. The display of the cytometric events can take a variety of formats. The events may be displayed all with the same color or different events may be displayed with different colors. For example, events within gate 902 can be one color whereas events outside of gate 902 can be a different color. A defined subset of the events, rather than all of the events, can be presented. In some cases, rather than illustrating the events themselves, the density of events can be displayed with different colors or contour lines.

Figure 9:
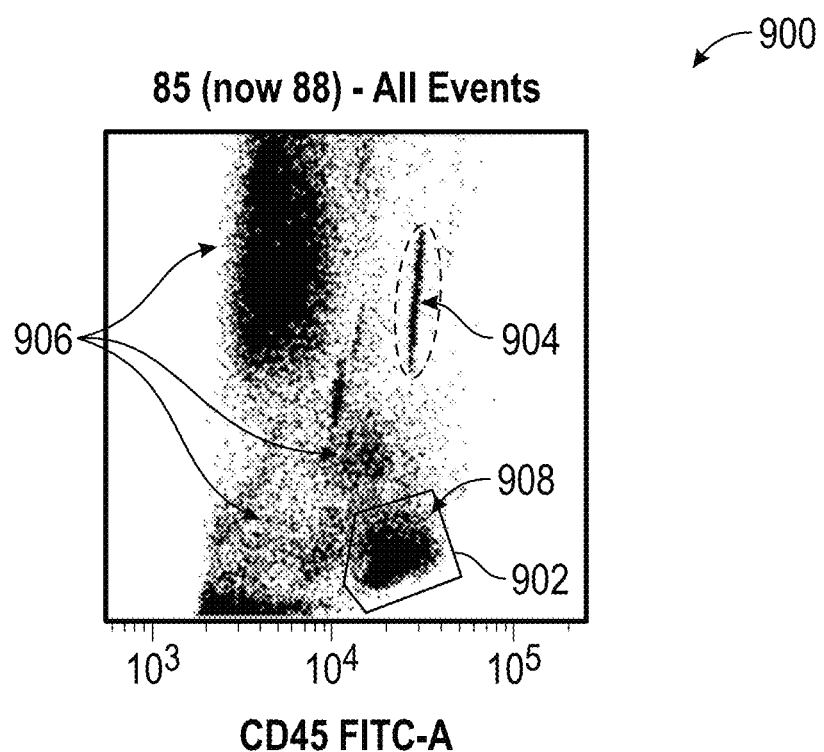
FIG. 9 shows an example of another dot-plot diagram including a gate.

Traditionally, when a user draws a gate around a set of events, the user uses a mouse to place vertices around a set of data points (by entering a "draw gate" mode and clicking on a series of points within the plot for example), which vertices are connected with lines by the display system as illustrated for the gate 902 in FIG. 9. The system may also have a "modify gate" mode where the user can move the mouse cursor to a vertex or line of a previously drawn gate, click and hold a mouse button, and then with the mouse button down move the mouse to drag the vertex or line to a new location to modify the gate. At different times during this gate drawing and modification process, it may be that different modes of presenting the event data on the display are more useful than others in allowing the user to produce an accurate gate boundary positioning. In conventional systems, the user has to switch back and forth between gate drawing/modifying activities and display selection activities. This slows down the gate drawing process.

In embodiments described below, user interaction with the system is improved by allowing automated or semi-automated simultaneous event data display format modification activities and gate drawing/modification activities. In some implementations, the system may automatically select a display format based on the characteristics of the event data (e.g., event density near the gate being drawn and/or modified) and/or the particular gate modification action being performed by the user. In other implementations, the user may be able to perform gate drawing/modification activities with one hand (e.g., in the traditional way with a mouse as described above) while simultaneously using a different input device (e.g., a keyboard) with their other hand to produce concurrent display modifications "on the fly" as the gate is being drawn/modified. In some implementations, the system may produce automated display changes as the user draws/modifies a gate, but those changes can be overridden, frozen, or otherwise modified by the user with the second input device. Such features make the gate drawing and modification process faster, more user-friendly, and more accurate.

Specific examples of various embodiments and systems in which they are implemented are described further below.

FIG. 1 shows a functional block diagram for one example of a graphics control system for analyzing and displaying cytometric events. A graphics controller 200 may be configured to implement a variety of processes for controlling graphic display of cytometric events.

A flow cytometer 102 may be configured to acquire flow cytometric events. For example, flow cytometer 102 may generate flow cytometric event data. The flow cytometer 102 may be configured to provide flow cytometric events to the graphics controller 200. A data communication channel may be included between the flow cytometer 102 and the graphics controller 200. The flow cytometric events may be provide to the graphics controller 200 via the data communication channel.

The graphics controller 200 may be configured to receive flow cytometric events from the flow cytometer 102. The flow cytometric events received from the flow cytometer 102 may include flow cytometric event data. The graphics controller 200 may be configured to provide a graphical display including a first plot of flow cytometric events to a display device 106. The graphics controller 200 may be further configured to render a gate around a population of flow cytometric events shown by the display device 106, overlaid upon the first plot. Additionally, the graphics controller 200 may be further configured to display the flow cytometric events on the display device 106 within the gate differently from other events in the flow cytometric events outside of the gate. For example, the graphics controller 200 may be configured to render the color of flow cytometric events contained within the gate to be distinct from the color of flow cytometric events outside of the gate. The display device 106 may be implemented as a monitor, a tablet computer, a smartphone, or other electronic device configured to present graphical interfaces.

The graphics controller 200 may be configured to receive a gate selection signal identifying the gate from a first input device. For example, the first input device may be implemented as a mouse 110. The mouse 110 may initiate a gate selection signal to the graphics controller 200 identifying the gate to be displayed on or manipulated via the display device 106 (e.g., by clicking on or in the desired gate when the cursor is positioned there).

After receiving the gate selection signal, the graphics controller 200 may be configured to receive a triggering event from a second input device. The second input device may be implemented as a keyboard 108. The keyboard 108 may control changes in plot visualization by sending a signal identifying a triggering event to the graphics controller 200. For example, activation of a specific key or group of keys on the keyboard 108 may generate a specific triggering event. In response to the triggering event, the graphics controller 200 may be configured to replace the first plot displayed on the display device 106 with a second plot while maintaining and/or manipulating the gate, for example, allowing a user to cycle through various plots of flow cytometric events while maintaining and/or manipulating a gate.

The first and second input devices may be implemented as one or more of the mouse 110, the keyboard 108, or other means for providing an input signal to the graphics controller 200 such as a touchscreen, a stylus, an optical detector, or a voice recognition system. Some input devices may include multiple inputting functions. In such implementations, the inputting functions may each be considered an input device. For example, as shown in FIG. 1, the mouse 110 includes a right mouse button 112 and a left mouse button 113, each of which may generate a triggering event.

The triggering event may cause the graphics controller 200 to alter the manner in which the data is displayed or which portions of the data is actually displayed on the display device 106 or both at the same time.

In some embodiments, the graphics controller 200 may be configured to detect when gate selection is initiated by the mouse 110. The graphics controller 200 may be further configured to automatically modify plot visualization to optimally facilitate the gating process. The modification may be based on the specific distribution of flow cytometric events received by the graphics controller 200.

The graphics controller 200 may be connected to a storage device 104. The storage device 104 may be configured to receive and store flow cytometric events from the graphics controller 200. The storage device 104 may also be configured to receive and store flow cytometric event data from the graphics controller 200. The storage device 104 may be further configured to allow retrieval of flow cytometric events and flow cytometric event data by the graphics controller 200.

A display device 106 may be configured to receive display data from the graphics controller 200. The display data may comprise plots of flow cytometric events and gates outlining sections of the plots. The display device 106 may be further configured to alter the information presented according to input received from the graphics controller 200 in conjunction with input from the flow cytometer 102, the storage device 104, the keyboard 108, and/or the mouse 110.

Figure 2:
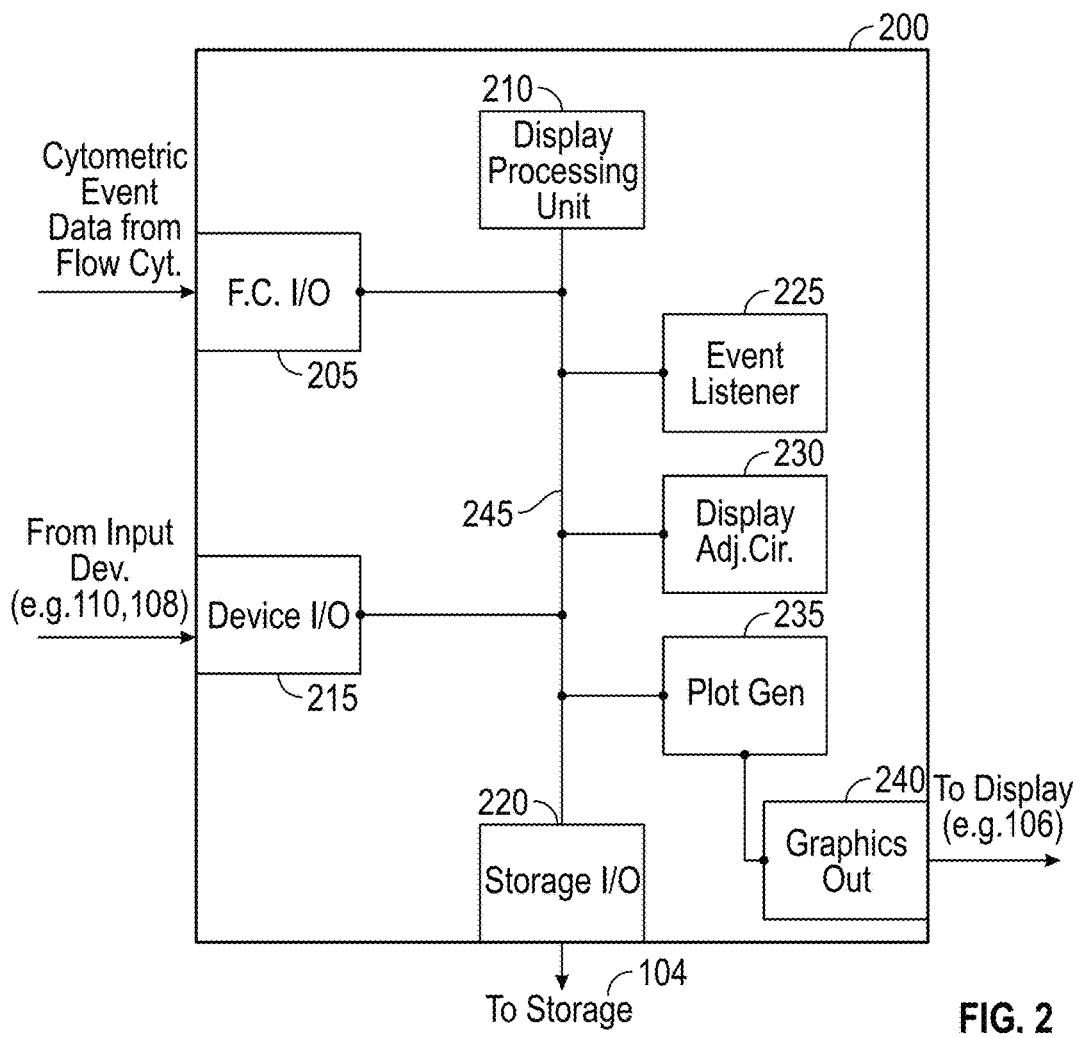
FIG. 2 shows a functional block diagram of an example of a graphics controller.

FIG. 2 shows a functional block diagram of an example of a graphics controller. The graphics controller 200 shown in FIG. 2 may be included in the system 100 shown in FIG. 1. The graphics controller 200 may be implemented as a specially configured device for dynamically adjusting a graphical display during cytometric data processing. In some implementations, the graphics controller 200 may be integrated with the flow cytometer 102, a display device 106 (e.g., tablet computer, laptop computer, desktop computer), or other electronic hardware.

The graphics controller 200 includes a flow cytometer input/output (I/O) interface 205. The flow cytometer input/output interface 205 is configured to receive cytometric event data from the flow cytometer, such as the flow cytometer 102 shown in FIG. 1. The flow cytometer I/O interface 205 may be a hardware interface providing a path for the event data to be received by the graphics controller 200. For example, the interface 205 may be implemented as a network interface, a Universal Serial Bus interface, a serial data communication interface, memory access device, or other machine-to-machine communication interface. The data may be received in a standardized, machine readable format such as a comma separated list, a token separated list, mark-up language document, or a spreadsheet.

The cytometric event data received by the graphics controller 200 via the flow cytometer input/output interface 205 may be stored in a storage device such as the storage device 104 shown in FIG. 1. The graphics controller 200 may include a storage input/output (I/O) interface 220 to facilitate storage and retrieval of data to and from a storage device. For example, the storage I/O interface 220 may be implemented as a network interface, a Universal Serial Bus interface, a serial data communication interface, memory access device, or other machine-to-machine communication interface. In some implementations, the storage I/O interface 220 may be configured to generate queries to retrieve information requested by an element of the graphics controller 200. Such queries may be in a standardized query language such as Structured Query Language (SQL). In some implementations, the storage I/O interface 220 may be configured to generate storage commands to persist data in the storage device. SQL update or insert commands are examples of storage commands generated by the storage I/O interface 220.

A display processing unit 210 is shown in FIG. 2. The display processing unit 210 coordinates the activities of the graphics controller 200. For example, the display processing unit 210 may receive a signal that data has been received via the flow cytometer I/O interface 205. Upon detecting the signal, the display processing unit 210 may transmit an instruction to route the data to the storage I/O interface 220 for storage. The display processing unit 210 may coordinate the activities according to a preconfigured set of machine readable instructions.

The graphics controller 200 shown in FIG. 2 also includes a device input/output (I/O) interface 215. The device I/O interface 215 receives signals from input devices such as a mouse or keyboard. The display processing unit 210 may detect an input signal and adjust a display as will be described in further detail. One input signal may include a message to begin displaying flow cytometric data. The input signal may include an identifier for the cytometric experiment for which data should be displayed. Using this identifier, the event data may be retrieved such as via the storage I/O interface 220 or from the flow cytometer via the flow cytometer I/O interface 205.

An event listener 225 may be included in the graphics controller 200 to monitor the signals received via the device I/O interface 215. The event listener 225 may be configured such that signals from input devices may be translated into graphics adjustments. The graphics controller 200 may include multiple event listeners 225 to account for different system contexts. For example, a key press before any event data is displayed may be used to trigger loading of data. However, once data is initially displayed, the same key press event may cause a different system response.

The event listener 225 may include a registry of events and corresponding graphics control functions to trigger upon detection of the event. For example, the event listener 225 may be configured to detect a keystroke (e.g., control key pressed with the "L" key and the "H" key). The event listener 225 may be contextually aware. For example, the keystroke may trigger the graphics control function when detected in conjunction with another input signal (e.g., mouse selection, mouse location), system state (e.g., power on, plugged-in), data state (e.g., cytometry data loaded), display state (e.g., plot displayed, type of plot currently displayed), or the like. The registry may be persisted in memory and accessed by the event listener 225.

Upon detecting an input event and identifying a system response, the event listener 225 may transmit an instruction to the appropriate element or elements of the graphics controller 200. For example, if the event indicates receipt of cytometric data, the event listener 225 may transmit a message to the storage I/O interface 220 to initiate storage of the received event data.

In some implementations, it may be advantageous to allow the display processing unit 210 to coordinate the system responses to detected events. This may be useful where multiple input signals may be received and arbitration is necessary to determine the order in which the events should be acted upon. The display processing unit 210 may be configured to manage the state changes using a state machine to represent the current status of the graphics controller 200 and possible next states.

Some events detected by the event listener 225 may be graphics control events. A display adjustment circuit 230 may be included to coordinate the adjustment of the graphic display of flow cytometric events from the current state to the adjusted state. The display adjustment circuit 230 may adjust the number of events displayed, the color of one or more events displayed, a plot type to use for displaying the events, the zoom level for the display, and the like.

The display adjustment circuit 230 may transmit the adjustments and an identification of the events to display to a plot generator 235. The plot generator 235 may in turn generate a computer displayable graphic representation of the event data according to the adjustments. The representation may then be provided to a display via a graphics output interface 240. The graphics output interface may be a video graphics array (VGA) interface, a high definition multimedia interface (HDMI), a wired or wireless network interface, or other communication means configured to provide graphics data, directly or indirectly, to a display device. In some implementations, the plot generator 235 may be configured to further select events to display based on the display adjustment(s) being applied.

The elements included in the graphics controller 200 may be coupled by a bus 245. The bus 245 may be a data bus, communication bus, or other bus mechanism to enable the various components of the graphics controller 200 to exchange information. It will further be appreciated that while different elements have been shown, multiple features may be combined into a single element, such as the display adjustment circuit 230 and the plot generator 235. Furthermore, additional elements may be included in the graphics controller 200 to support the features described. For example, a power source is not shown but may be included to provide power for the graphics controller 200. This can allow the graphics controller 200 to operate as a standalone graphics control hub to receive data from one or more cytometers, receive inputs from one or more input devices, and provide graphics to one or more display sources.

Figure 3:
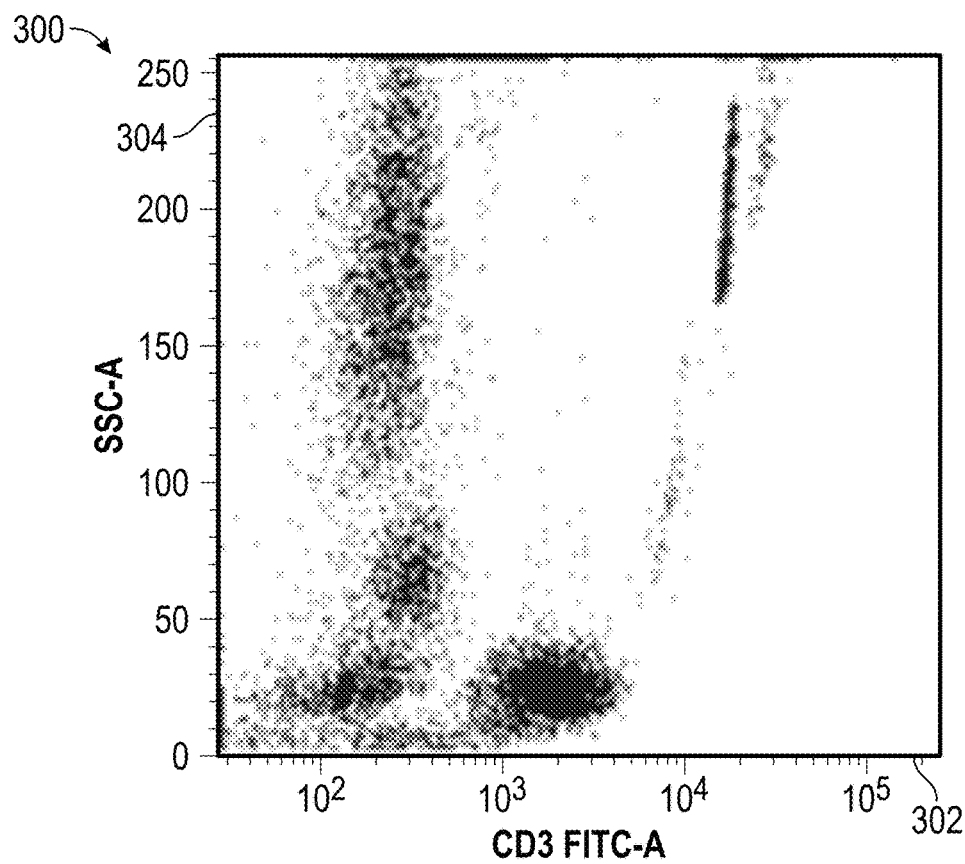
FIG. 3 shows an example of a dot-plot diagram.

FIG. 3 shows an example of a dot-plot diagram. The dot-plot 300 displays a scatter plot of the events along an x-axis 302 and a y-axis 304. The x-axis 302 illustrates the parameter of interest. In the example shown in FIG. 3, the x-axis 302 represents light intensity for FITC-A labeled CD3 antibodies. The y-axis 304 shows the side scatter count (SSC). The side scatter count may be referred to as events or event count. The dot-plot 300 is one example of a representation of cytometric data that may be generated by the plot generator 235.

The plot can be drawn such that several populations of data are identified. Each population may be represented using a unique color. An advantage of the dot-plot 300 is that populations can be readily distinguished from one another visually. This can be useful when comparing different data sets. One significant disadvantage of the dot-plot 300 is that the diagram does not include information about how dense the data is. In addition, the dot-plot 300 can be saturated when there are a large number e.g., hundreds of thousands of events. This may lead to a loss of fidelity of clusters which may be co-located or closely located. To help provide density information, one or more of the other plot types may be used.

Each dot in a dot-plot may represent a biological object, often a cell. These cells are distributed more densely in some areas, less densely in other areas. A cluster of closely located dots often represents cells of certain type, called a population. The goal of the specialist processing these data is to establish limits of these populations by specifying geometrical borders around them. Such borders are called gates, and the processing of establishing or adjusting them is gating.

The gating can be performed automatically by software algorithms, or manually by a human; or it may be initially performed automatically and then adjusted manually. In manual gating, the operator draws or adjusts the gates by clicking the plot with computer mouse and dragging the mouse.

Figure 4:
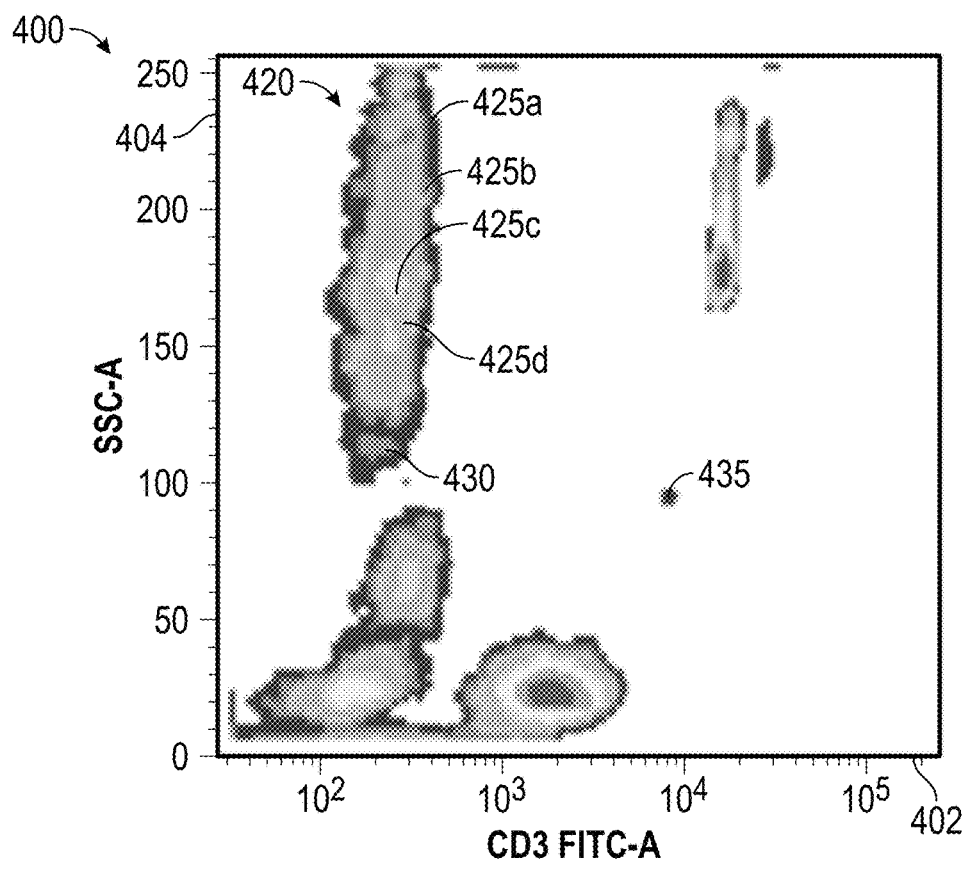
FIG. 4 shows an example of a 2D density plot diagram.

FIG. 4 shows an example of a 2D density plot diagram. The 2D density plot diagram 400 shows the density of data using two parameters plotted against each other. As with FIG. 3, an x-axis 402 shows the parameter values while a y-axis 404 illustrates the side scatter level. Additionally, the 2D density plot diagram 400 can include density information for areas in the diagram. For example, the 2D density plot diagram 400 includes a cluster of data 420. The cluster of data 420 may include several regions, each region associated with a common density. As shown in FIG. 4, four regions 425a, 425b, 425c, and 425d are shown. In some implementations, each region may be graphically presented using a different color. The 2D density plot diagram 400 is another example of a representation of cytometric data that may be generated by the plot generator 235.

While the 2D density plot diagram 400 provides context for the related densities, the density information is presented in a relatively raw format. As such, visual artifacts may be included in the representation. As shown in FIG. 4, a pocket 430 of a data at a given density may be formed. A cluster 435 of outliers is also shown in FIG. 4. These artifacts in the 2D density plot diagram 400 may be due to noise, calibration error, or other characteristics of the data. As with the dot-plot diagram 300, the 2D density plot diagram 400 may undergo gating and/or include gates to identify populations of interest.

Figure 5:
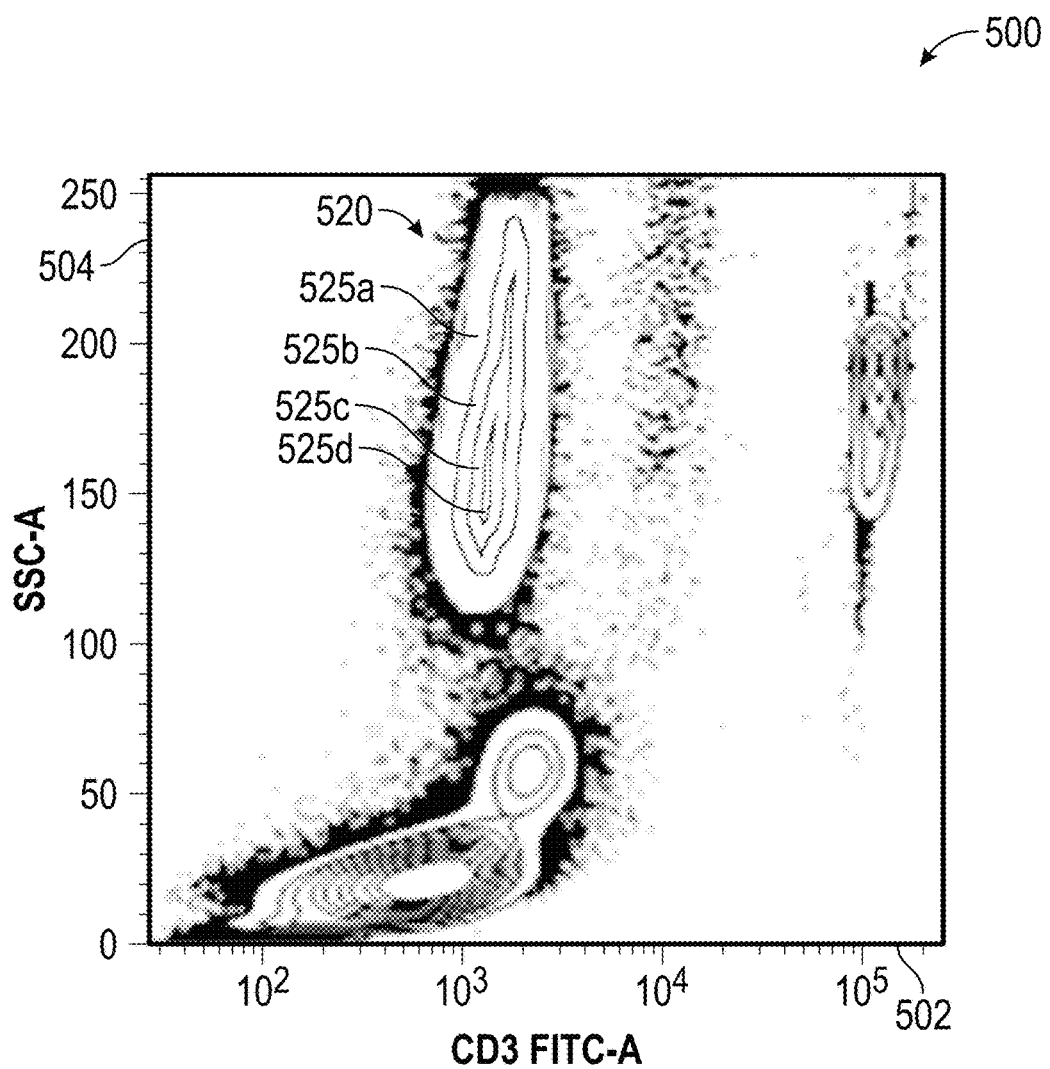
FIG. 5 shows an example of a contour plot diagram.

FIG. 5 shows an example of a contour plot diagram. The contour plot diagram 500, like the 2D density plot diagram 400, provides a visual representation useful for making sense of the data in a plot of flow cytometry data. The contour plot diagram 500 can be a better choice for display of the data because the contour plot diagram 400 uses less memory than the 2D density plot diagram 400. Furthermore, contour plot diagrams generally smooth the distracting visual artifacts discussed in reference to the 2D density plot diagram 400. The contour plot diagram 500 is another example of a representation of cytometric data that may be generated by the plot generator 235.

The contour plot diagram 500 shown in FIG. 5 includes an x-axis 502 showing the parameter values and a y-axis 504 illustrating the side scatter count level. Additionally, the contour plot diagram 500 can include density information for areas in the diagram. For example, the contour plot diagram 500 includes a cluster of data 520. The cluster of data 520 may include several regions, each region associated with a common density. In FIG. 5, four regions 525a, 525b, 525c, and 525d are shown. In some implementations, each region may be graphically presented using a different color.

The contour plot diagram 500 is a tool that allows the display of two dimensional data. It uses a two-dimensional array of values that contain the event counts for the histogram. What makes the contour useful is that a series of contours (e.g., slices) in the z-direction are made that show the levels of the data. This is a similar process as is used to create a topological map. Each level may then be assigned a color or other visual discriminator. The resulting display is a collection of polygons that may be colored according to the level of the data. As with the dot-plot diagram 300, the contour plot diagram 500 may undergo gating and/or include gates to identify populations of interest.

For each of the plots described, it is possible to adjust the display of the plot to, for instance, provide a more accurate view of the events being gated. For example, the density of the dots in a given plot may be so high that the operator cannot see clearing between the clusters.

Figure 6A:
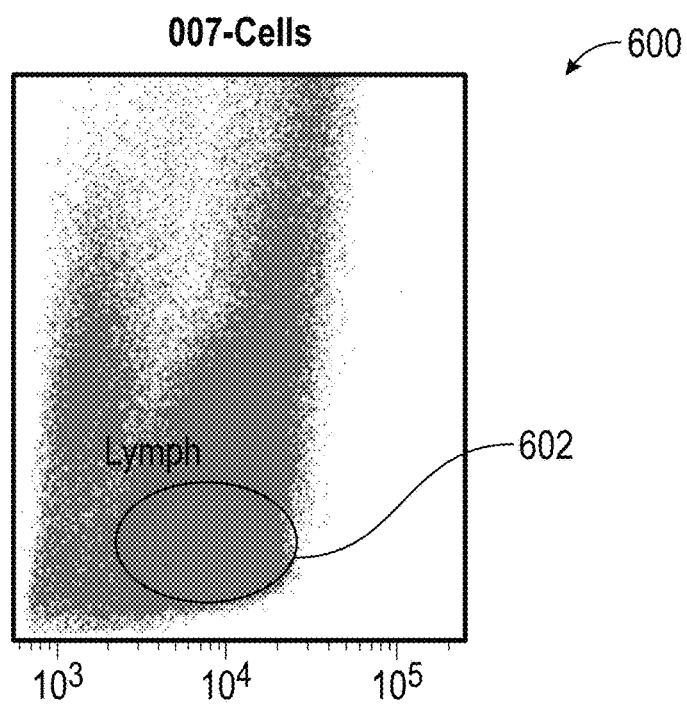
FIG. 6A is a dot-plot diagram illustrating an example of a dense dot-plot diagram.

FIG. 6A is a dot-plot diagram illustrating an example of a dense dot-plot diagram. The dense dot-plot diagram 600 includes a population 602 that is not displayed with any discernable distinction from the other cytometric events included in the plot. Dense in this sense is used to indicate the number of events in a specified area of the display.

To perform gating in such situation, the plot display may be adjusted. For example, the plot may be resized to be bigger. Manual gating can then be performed on the zoomed-in display, then the plot resized to the initial size. Another adjustment may be to change the properties of the dense dot-plot diagram 600 to display only a certain fraction of the dots.

Figure 6B:
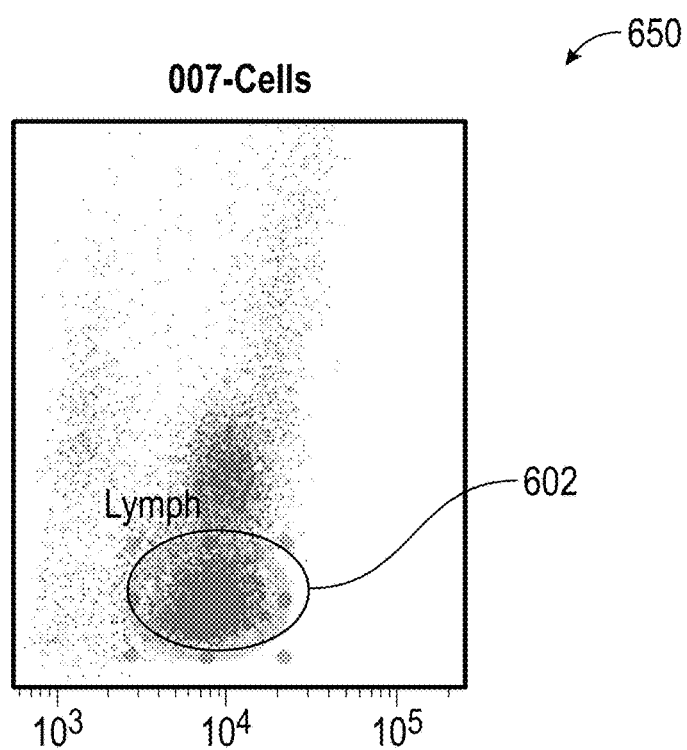
FIG. 6B is a dot-plot diagram illustrating an example of a reduced density dot-plot diagram of the events shown in FIG. 6A.

FIG. 6B is a dot-plot diagram illustrating an example of a reduced density dot-plot diagram of the events shown in FIG. 6A. In the reduced density dot-plot diagram 650, the population 602 is more clearly visible to a user as distinct from other cytometric events.

Another display adjustment may include switching plot type. For example, the initial plot displayed may be adjusted to display the same data as a density plot or a contour plot, such as those shown in FIG. 4 and FIG. 5, respectively. Often the operator has to alternate between the different plot types. Each of such operations interrupts the continuity of the gating process, makes it less efficient. The system described herein can identify optimal plot views to present for a given data set in anticipation of gating activities and adjust the display accordingly.

Another display adjustment may include changing a property of a given plot. For example, during gating, gated dots are sometimes shown in a different color than the other dots included in the display. This can distort perception of where exactly the gate should be located. To overcome the distortion, the system can change colors of the populations during the gating and then restore the original colors once gating is completed.

The features described facilitate the display adjustments such as the examples discussed above.

Figure 7:
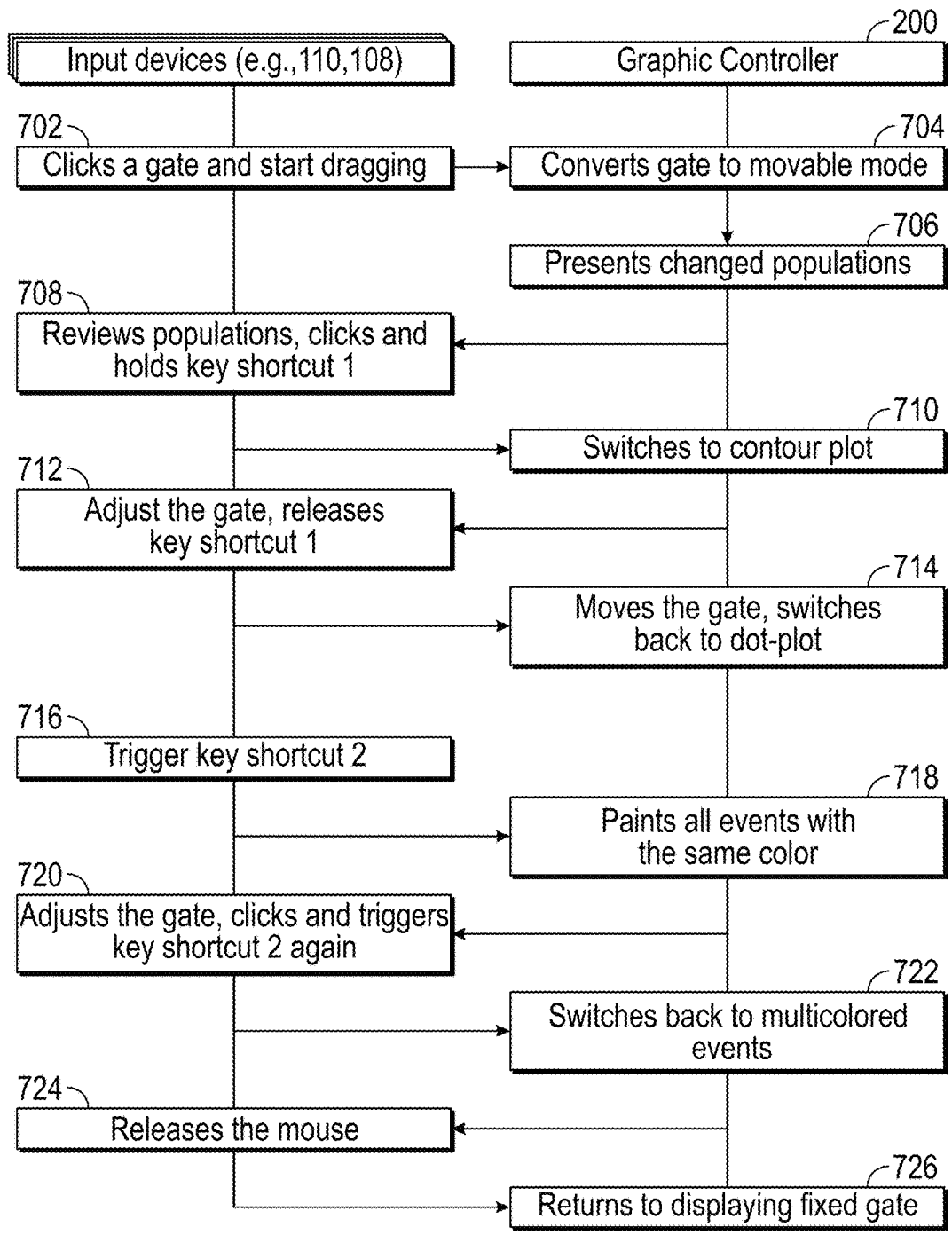
FIG. 7 is a message flow diagram of an example method of display adjustment.

FIG. 7 is a message flow diagram of an example method of display adjustment. The message flow may be implemented in whole or in part by one or more of the devices described, such as those shown in FIG. 1 or FIG. 2. For illustrative purposes, input devices and the graphics controller 200 are shown. In describing FIG. 7, reference will be made to a mouse and keyboard inputs. It will be understood that these input signals may be provided by alternative input devices such as those discussed with reference to FIG. 1.

In the message flow diagram of FIG. 7, an operator may trigger changes to the display by activating different keys on the keyboard, while holding the mouse pressed down. The graphics controller 200 detects the input signals and adjusts the display accordingly. In this way, the described features make it possible to alternate between different representations of the plot almost instantly, and without disrupting the continuity of the gating process.

At block 702, a gate is activated via a click event from an input device such as a mouse. In some implementations, the gate may be activated by another input such as a key-press, touch on a touchscreen, gesture, voice command, or a combination thereof. The activation may be detected by the computer system by mapping a location of a pointer (e.g., cursor) proximate to the location of a gate presented on a graphic display of cytometric event data. The activation is generally associated with adjustment of a previously rendered gate.

At block 704, the gate is identified as being adjustable. The graphics controller 200 may change the visual representation of the gate to indicate activation. Changes may include changing the color or size of lines or points representing the gate.

As the gate is adjusted, at block 706, changed populations are presented. Because when the gate vertices are moved, there may be different events inside the gate. Accordingly, these different events may be colored distinctly such as by changing the color of the population included in the gate.

At block 708, a first key shortcut is triggered. The first key shortcut may be triggered while a gate is still activated, such as described with reference to block 702. A key shortcut generally refers to a display setting stored by the system. The display setting includes an activation event and one or more plot characteristics to apply upon detection of the event. For example, a display setting may indicate a plot display size, a plot type, event display coloring (e.g., color to use for displaying events), event display size (e.g., size of marker to use for each event), or a quantity of events to display. The quantity of events to display may be specified in absolute terms (e.g., 10,000 events), a percentage of total events, or a density of events.

At block 710, the graphics controller 200, having detected the two input signals, gate activation and first key shortcut, switches the graphic representation using the display setting. The graphics controller 200 then generates a second plot to replace the currently displayed plot and provides the second plot for display.

At block 712, the gate may be further adjusted, this time with the benefit of the second plot rather than the initial plot. After the adjustment is performed, block 712 includes detecting the key shortcut being released. The release may indicate to the system that the graphic adjustments previously applied should be removed.

At block 714, the graphics controller 200 receives one input signal indicating gate adjustment. Having no longer detected the adjustment key shortcut, the graphics controller 200 switches the graphic representation to return to the initial setting (e.g., prior to the adjustment applied in block 710). The graphics controller 200 replaces the currently displayed plot and provides the reverted plot for display. The reverted plot will include the new gate location without the display setting applied to the underlying plot.

The adjustment described with reference to blocks 702 through 714 may be referred to as a hold adjustment. A hold adjustment may refer to an adjustment to the visual display that persists while the activation event (e.g., key shortcut press) is detected. Once the activation event is no longer detected, the adjustment(s) associated with the activation event are removed and the plot display reverts to the pre-hold state.

Another adjustment which may be implemented may be referred to as a switched adjustment. A switched adjustment may refer to an adjustment to the visual display that can be switched on and off upon detection of the activation event. Switched adjustments may have a default initial state and then, upon detection of the activation event, switch to the alternate state. Blocks 716 through 726, illustrate a switched adjustment.

At block 716, a second key shortcut is triggered. The second key shortcut may be triggered while a gate is still activated, such as described with reference to block 702. At block 718, the graphics controller 200 receives the key shortcut. As shown in FIG. 7, the second key shortcut is associated with display settings that cause a change in the color of events plotted such that all events are plotted with the same color. The graphics controller 200 prepares a plot according the display settings for the second key shortcut and provides this for display. In some implementations, the graphics controller 200 may store the display settings of the graphic display in memory prior to the adjustment such that the plot can be reverted to the pre-adjusted state.

At block 720, the gate may be adjusted and the second key shortcut may again be triggered. The graphics controller 200 is configured to receive the adjustments and the triggering of the second key shortcut. The graphics controller 200 may then undo the display adjustment for the second key shortcut, reverting to the pre-adjusted state. The pre-adjusted state may be retrieved from memory.

At block 724, the gate activation may terminate. The termination of gate activation may be indicated by the release of a mouse button or other signal from an input device. At block 726, the graphics controller 200 may detect the termination of the gate activation. Upon detection, the graphics controller 200 may adjust the visual representation of the gate to indicate activation. Changes may include changing the color or size of lines or points representing the gate or changing the color of the population included in the gate.

In some implementations, the graphics controller 200 may be configured to generate graphics displays for multiple workstations. In such implementations, the messages may include a workstation identifier. The workstation identifier may be used to identify a user operating a workstation. The user at a first workstation may have defined custom display settings. For example, a color blind person may desire color pallets which can be seen. In some implementations, an identifier for the user may be provided in the messaging. In such implementations, display settings may be associated with an identified workstation or user. Other characteristics may be used to select display settings. For example, the type of data plotted may be used to identify display settings whereby a three-factor experiment may be associated with a first set of display settings while a four-factor experiment may be associated with a second set of display settings.

FIG. 7 illustrates input signal driven adjustments. In some implementations, characteristics of the gated population or an overall characteristic of the flow cytometric events may be used to identify adjustments.

Figure 8:
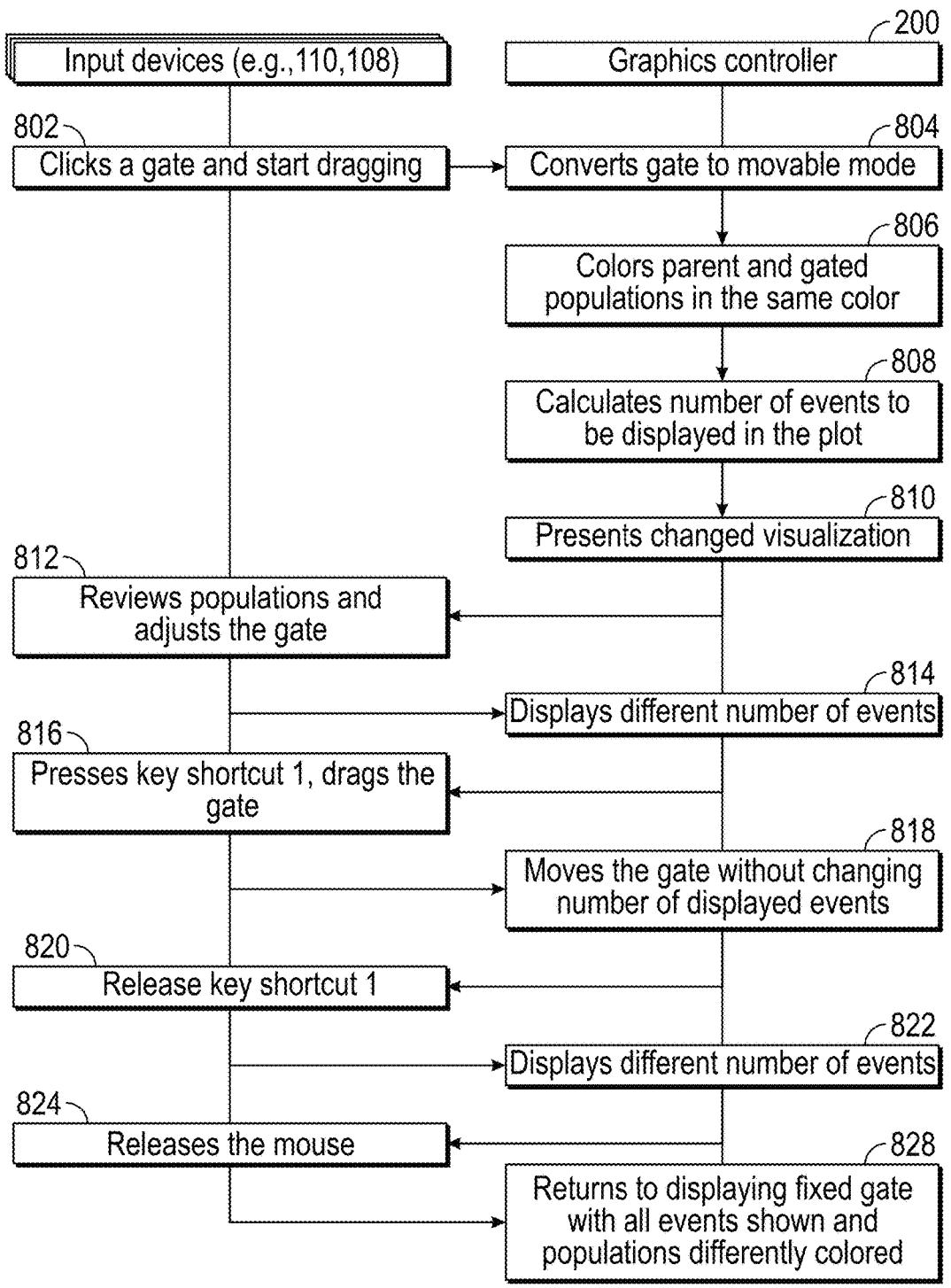
FIG. 8 is a message flow diagram of another example method of display adjustment.

FIG. 8 is a message flow diagram of another example method of display adjustment. The message flow may be implemented in whole or in part by one or more of the devices described, such as those shown in FIG. 1 or FIG. 2. For illustrative purposes, input devices and the graphics controller 200 are shown. In describing FIG. 8, reference will be made to a mouse and keyboard inputs. It will be understood that these input signals may be provided by alternative input devices such as those discussed with reference to FIG. 1.

In the embodiment shown in FIG. 8, the graphics controller 200 is configured to detect when the gate adjustment by mouse is started, and automatically adjust plot visualization to optimally facilitate the gating process. The adjustment may depend on specific distribution of events (e.g., dots plotted) and on the gate size and location. The display may change gradually when the gate is being moved or its shape transformed.

The feature discussed with reference to FIG. 8 may be implemented in conjunction with or as an alternative to those described in FIG. 7. For example, an input device may transmit a signal to control whether the automatic changes are applied, whether they are being modified continuously or fixed, or which visualization algorithm to be invoked such as by pressing different keys on the keyboard.

Similar to blocks 702 and 704 in FIG. 7, at block 802, a gate is activated via a click from a mouse and, at block 804, the gate is identified as being adjustable. Upon detecting the activation of the gate, the graphics controller 200 may be further configured to adjust display of the plot. As shown in FIG. 8, at block 806, the graphics controller 200 is configured to identify a display setting which causes events in the parent and gated populations to be plotted using the same color.

At block 808, the number of events to display in the plot may also be adjusted by the same or a second display setting. Calculation of the number of events to show may include sequentially selecting events, from the flow cytometry events. The sequence may be according to sequence numbers associated with each event, beginning with the first sequence number until the quantity of events is obtained. In some implementations, the calculation may include randomly selecting events, from the flow cytometry events, until the quantity of events is obtained. In some implementations, the calculation may include selecting via uniform sampling of the flow cytometry events until the quantity of events is obtained.

At block 810, a plot of the events is generated which presents the changed visualization according to the identified display setting or settings. At block 812, the updated representation of the events is presented and further adjustments to the gate are performed. Adjustments to the gate may include increasing the area encompassed by the gate, decreasing the area encompassed by the gate, or moving the gate from a first location to a second location. Any of these adjustments may change the number of events included within the gated area. As such, the display goals (e.g., number of events, density of events, etc.) met by a first display adjustment may not be satisfied when the gate is changed.

At block 814, the graphics controller 200 receives the input signal indicating the further changes to the gate and determines a new number of events to display via a plot. The determination may include a similar calculation as described with reference to block 808. A plot of the events is generated which presents the changed visualization according to the identified display setting or settings.

At block 816, the gate may be activated for a move while a second input signal is received. The input signals are provided to the graphics controller at block 818. Unlike block 814, at block 818, the graphics controller receives the gate adjustment input signal along with a key shortcut input signal. As shown, the key shortcut input signal may configure the graphics controller 200 to suppress re-evaluation of the number of events to display. In such an implementation, the representation of the events is maintained with only a change in the location of the gate presented.

At block 820, while maintaining the gate activation, the key shortcut input signal may be terminated. At block 822, the graphics controller 200 detects the gate activation without the key shortcut. In response, the graphics controller 200 re-evaluates the number of events to display based on the new gate location. Once the number of events to display is determined, graphics controller 200 generates a new plot including the new number of.

At block 824, the activation of the gate is terminated. As shown, the termination of the gate activation may be signaled by the release of a mouse button. Similar to block 726, at block 828, the graphics controller 200 may adjust the visual representation of the gate to indicate activation. Changes may include changing the color or size of lines or points representing the gate or changing the color of the population included in the gate.

As with FIG. 7, the messaging shown in FIG. 8 may be performed for multiple workstations, experiment types, users, or combinations thereof.

FIG. 9 shows an example of another dot-plot diagram including a gate. In the plot 900 the gate 902 surrounds a first population 908. The plot 900 also includes a second population 904 which is not gated. Additional ungated events 906 are also shown.

When the plot 900 is initially presented, the events within the first population 908 may be presented in a first color, the events within the second population 904 may be presented in a second color, and the ungated events 906 may be presented in a third color. It may be desirable for the first color, second color, and third color to be different colors.

Upon activation of the gate 902, the graphics controller 200 may prepare a second plot to change the color of the events such that events within the gate (e.g., the first population 908) and the ungated events 906 may be rendered with the same color. This change may, in some implementations, provide a visual display amiable to adjusting the gate 902. Another non-limiting advantage of this change is to preserve distinctions between ungated events (e.g., the ungated events 906) and other populations shown in the plot such as the second population 904. Once the gate is deactivated, the graphics controller 200 may return to the three-color display. Thus, the graphics controller 200 may change only the color of the gated population and other ungated events to the predetermined color that is strongly distinctive from the background color and colors of other populations.

In another implementation, once the gate is activated, all events are displayed monochromatically. The application of such color adjustments may be triggered when the graphics controller 200 detects the gate activation along with a second triggering event such as a key shortcut, gesture, or other input signal. Display settings may be defined for the system, for the user, for the experiment, or some combination thereof to control how the graphics controller 200 should adjust the display. By changing the color of all the events to the same color, good contrast to the background can be provided by the system.

Figure 10:
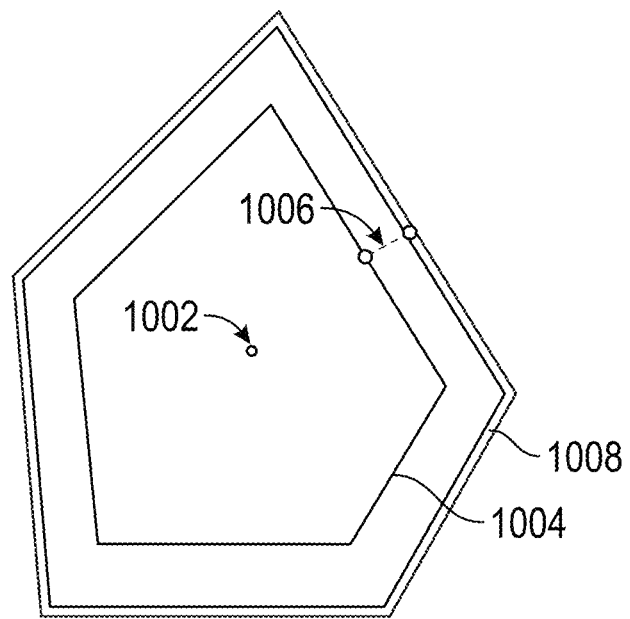
FIG. 10 is a gate diagram showing an example of an area identification for a gate.

FIG. 10 is a gate diagram showing an example of identification of a representative area for a gate. The representative area can be used to determine how many events to display for a given plot. The number of events to show in the entire plot may be determined such that in the representative area, a certain portion (e.g., 50% of the area) of the area is covered with events.

The identification of the representative area (expanded area 1008) begins with the identification of a gate 1004. For the gate 1004, there may be a center point 1002 which is the most central location for the gated population. It may be desirable to change the number of events displayed to focus on the events of the gated area. However, limiting the adjustment to just the gated area may not afford adequate detail to permit a visual distinction for the margins and/or bounds of the population of events shown in the graphic representation.

Accordingly, the expanded area 1008 may be identified by increasing the area of the gate 1004 to encompass an area which includes the desired margins of the population. As shown, an expansion amount 1006 is determined. As shown in FIG. 10, the center point 1002 remains the same, but the polygon formed by the gate 1004 is increased in size to yield the expanded area 1008.

Using the identified area within the polygon 1108, the number of events shown for the plot may be adjusted such that a certain portion (e.g., 50% of the area) of the identified area is covered with events.

Figure 11:
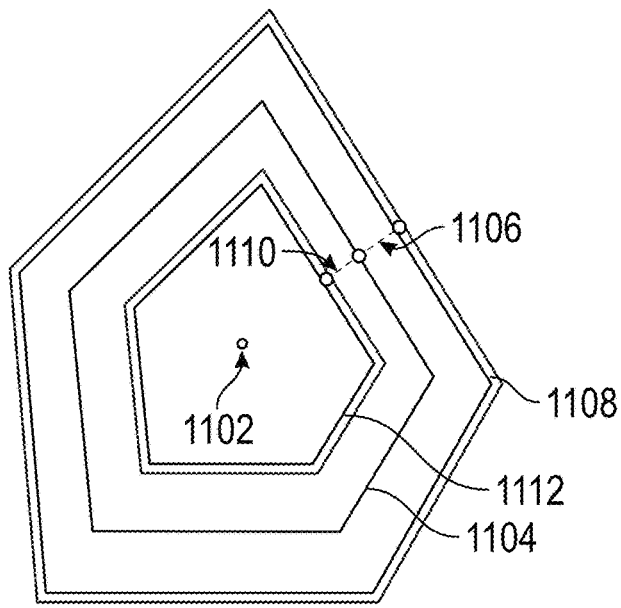
FIG. 11 is a gate diagram showing another example of an area identification for a gate.

FIG. 11 is a gate diagram showing another example of an area identification for a gate. Where in FIG. 10 the gate 1004 was expanded, in FIG. 11, a more localized adjustment may be performed such that only the events displayed in the area near the gate 1104 are taken into account when calculating desired density of displaying events. Using the gate 1104 polygon, the size is increased by a first amount 1106 (e.g., 33%, 19%, 2%), so that the center remains the same, and is also decreased by a second amount 1110 (e.g., 33%, 13%, 7%). The area between the "inflated" polygon 1108 and the "deflated" polygon 1112 is the representative area.

Using the identified area between the polygons 1108 and 1112, the number of events shown for the plot may be adjusted such that a certain portion (e.g., 50% of the area) of the identified area is covered with events.

In some implementations, when adjusting the number of events to display, the cytometric data may not include enough events within the area of interest to show the target quantity of events. In such implementations, if all events are shown for the identified area, if the covered fraction of the representative area is significantly below the target value (for example, the target fraction is 50%, but only 10% of the area is covered), the graphics controller 200 may be configured to adjust the display by increasing size of the dots representing the events, to get closer to the target coverage value.

Figure 12:
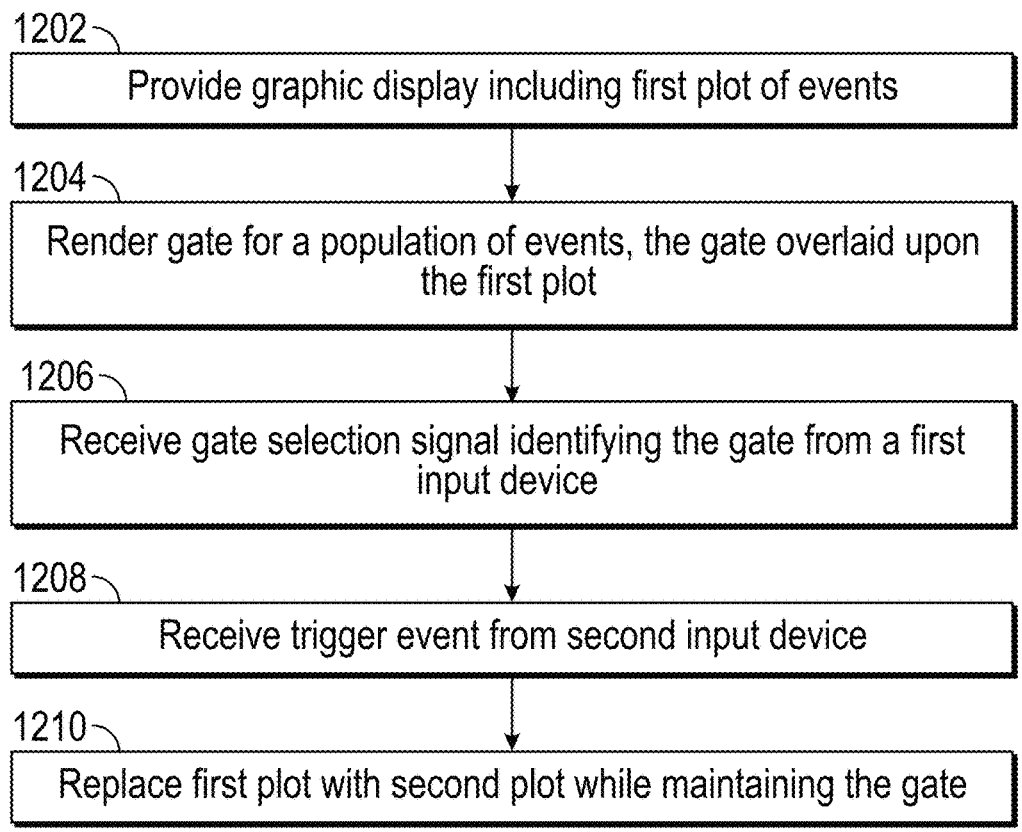
FIG. 12 is a process flow diagram of an example method of controlling graphic display of cytometric events.

FIG. 12 is a process flow diagram of an example method of controlling graphic display of cytometric events. The method shown in FIG. 12 may be implemented in whole or in part by one or more of the devices discussed above, such as in relation to FIG. 1 and FIG. 2.

The method begins at block 1202 by providing a graphic display including a first plot of flow cytometry events. Providing the graphic display may include transmitting a machine-readable representation of the plot. The representation may include instructions to paint pixels, polygons, or other visual indicators at specific locations on a display device. The instructions may indicate one or more of color or size for presenting the visual indicator.

At block 1204, a gate is rendered around a population of cytometric events shown by the graphic display. In rendering the gate, the gate is overlaid upon the first plot. Rendering the gate may include transmitting a machine-readable representation of the gate. The representation may include instructions to paint pixels, polygons, or other visual indicators at specific locations on a display device. The instructions may indicate one or more of color or size for presenting the visual indicator.

At block 1206, a gate selection signal is received. The gate selection signal identifies the gate from a first input device. For example, the gate may be selected by a mouse click. The selection signal may be received via wired or wireless means to provide an indication of what input device transmitted the selection and, in some implementations, what has been selected. The indication of what was selected may be a location identifier. In such implementations, the graphics controller 200 may be configured to use the location identifier to determine which gate was selected. In some implementation, the indication may be a gate identifier. The gate identifier may be a unique identifier indicating a specific gated population. Where the graphics controller 200 is configured to multiple hosts, the gate selection signal may also include an identifier for the workstation or user from which the selection signal was transmitted.

While the gate is selected, the method, at block 1208, includes receiving a triggering event from a second input device. For example, a key shortcut may be received from a keyboard. Where the graphics controller 200 is configured to multiple hosts, the gate triggering event may also include an identifier for the workstation or user from which the selection signal was transmitted.

At block 1210, in response to said triggering event, the first plot is replaced with a second plot while maintaining and/or modifying the gate on the graphic display. In some implementations, the plot (e.g., dot-plot) may be a separate display layer from a layer including the gate. Replacing the first plot may include removing the layer for the first plot and inserting a new layer beneath the gate with the second plot. Other graphic representations may be used to switch from the first plot to the second plot.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed graphics processor, which may include one or more processors, such as one or more digital signal processors (DSPs), configurable microprocessors, an application specific integrated circuits (ASICs), field programmable logic arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a specialized graphic control card.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A graphics control device for display of cytometric events, the graphics control device comprising:
   an input device port configured to receive messages from input devices;
   an event listener in data communication with the input device port, the event listener configured process the messages received from the input devices;
   a computer-readable memory storing executable instructions; and
   one or more computer processors in communication with the computer-readable memory, wherein the one or more computer processors are configured to execute the executable instructions to at least:
      provide a graphic display including a first plot of flow cytometry events;
      receive, from a first input device via the input device port, a first selection identifying a first area of the first plot including a first population of cytometric events at a first time and a second selection identifying a second area of the first plot including a second population of cytometric events at a second time; and
      between the first time and the second time:
         receive, from a second input device via the input device port, a triggering event associated with a graphics display adjustment,
         generate a second plot based at least in part on the first plot and the graphics display adjustment, and
         replace the first plot with a second plot on the graphics display while displaying the second selection.

2. The graphics control device of claim 1, further comprising a memory storing a display setting for graphically plotting events upon receipt of a message including a triggering event, the display setting indicating at least one of: a plot display size, a plot type, event display coloring, or a quantity of events to display; and
   wherein the one or more computer processors are configured to execute the executable instructions to at least:
      retrieve the display setting for the triggering event; and
      generate the computer displayable graphic representation using the display setting.

3. The graphics control device of claim 2, wherein the memory is configured to store the display setting further indicating a target event display density, and wherein the one or more computer processors are configured to execute the executable instructions to at least generate the computer displayable graphic representation including a display of the flow cytometric events according to the target event display density.

4. The graphics control device of claim 1, wherein the one or more computer processors are configured to execute the executable instructions to at least:
   present events within the gate for display according to a first display setting via the first plot; and present all events of the flow cytometry events for display according to a second display setting via the second plot.

5. The graphics control device of claim 4, wherein the one or more computer processors are configured to execute the executable instructions to at least:
present the events within the gate for display according to the first display setting by presenting the events within the gate differently from other events in the flow cytometry events via the first plot.

6. The graphics control device of claim 1, wherein the one or more computer processors are configured to execute the executable instructions to at least:
in response to a triggering event, generate an expanded area by expanding the second area of the first plot by an expansion factor;
identify a quantity of events to display via the second plot such that events displayed within the expanded area match a target event display density;
select the quantity of events; and
include a visual indicator for each event selected on the second plot.

7. The graphics control device of claim 6, wherein the one or more computer processors are configured to execute the executable instructions to at least generate a reduction area by reducing the second area of the first plot by a reduction factor, wherein an area between the expanded area and the reduction area includes events displayed at the target event display density via the second plot.

8. The graphics control device of claim 6, wherein each event included in the flow cytometry events is associated with a sequence number, and wherein the one or more computer processors are configured to execute the executable instructions to at least select the quantity of events comprises sequentially selecting events, from the flow cytometry events, beginning with the first sequence number until the quantity of events is obtained.

9. The graphics control device of claim 6, wherein the one or more computer processors are configured to execute the executable instructions to select the quantity of events includes executable instruction to at least:
randomly select events, from the flow cytometry events, until the quantity of events is obtained; or
select via uniform sampling of the flow cytometry events until the quantity of events is obtained.

10. The graphics control device of claim 8, wherein the flow cytometry data does not include enough events to reach the quantity, and wherein the one or more computer processors are configured to execute the executable instructions to increase the size of visual indicators for events within the second selection such that the second area matches the target event display density for the second plot.

11. A method of controlling graphic display of cytometric events, the method comprising:
providing a graphic display including a first plot of flow cytometry events;
receiving, from a first input device at a first time, a first gate selection signal identifying a first area of the first plot including a first population of flow cytometry events;
receiving, from the first input device at a second time after the first time, a second gate selection signal identifying a second area of the first plot including a second population of flow cytometry events; and
between the first time and the second time:
receiving a triggering event from a second input device; and
in response to said triggering event, replacing the first plot with a second plot while displaying a gate identified by the second selection signal overlaid on the second plot.

12. The method of claim 11, further comprising retrieving a display setting for graphically plotting events upon receipt of the triggering event, and
wherein replacing the first plot with the second plot comprises:
obtaining the display setting for the triggering event; and
generating the second plot using the display setting, and
wherein the display setting indicates at least one of: a plot display size, a plot type, event display coloring, or a quantity of events to display.

13. The method of claim 12, wherein:
the display setting further indicates a target event display density;
the target event display density is less than or equal to a density of events shown in the first plot; and
generating the second plot includes a display of the flow cytometric events according to the target event display density.

14. The method of claim 11, wherein:
events within the gate are displayed according to a first display setting via the first plot; and
all events of the flow cytometry events are displayed according to a second display setting via the second plot.

15. The method of claim 11, wherein displaying the events within the gate according to a first display setting comprises displaying the events within the gate differently from other events in the flow cytometry events.

16. The method of claim 11, further comprising:
in further response to said triggering event, generating an expanded area by expanding the second area by an expansion factor;
identifying a quantity of events to display via the second plot such that events displayed within the expanded area match a target event display density;
selecting the quantity of events; and
including a visual indicator for each event selected on the second plot.

17. The method of claim 16, further comprising generating a reduction area by reducing the second area of the first plot by a reduction factor, wherein an area between the expanded area and the reduction area includes events displayed at the target event display density via the second plot.

18. The method of claim 16, wherein selecting the quantity of events comprises one of:
randomly selecting events, from the flow cytometry events, until the quantity of events is obtained; or
selecting via uniform sampling of the flow cytometry events until the quantity of events is obtained.

19. The method of claim 16, wherein the flow cytometry data does not include enough events to reach the quantity, and wherein including the visual indicator includes increasing the size of visual indicators for events within the second selection such that an event display density for the second area matches the target event display density via the second plot.

20. An apparatus comprising:
a flow cytometer configured to acquire flow cytometric events;
one or more processors in communication with the flow cytometer, the one or more processors configured to:

provide a graphic display including a first plot of flow cytometry events;
receive, from a first input device at a first time, a first gate selection signal identifying a first area of the first plot including a first population of flow cytometry events;
receive, from the first input device at a second time after the first time, a second gate selection signal identifying a second area of the first plot including a second population of flow cytometry events; and
between the first time and the second time:
   receive a triggering event from a second input device; and
   in response to said triggering event, replace the first plot with a second plot while displaying a gate identified by the second selection signal overlaid on the second plot.

* * * * *